United States Patent [19]

Galbraith

[11] 4,286,064

[45] Aug. 25, 1981

[54] PROCESS FOR ISOLATING ACTIVE DEBRIDING AGENT FROM BROMELAIN

[75] Inventor: William Galbraith, Newark, Del.

[73] Assignee: Riker Laboratories, Inc., Northridge, Calif.

[21] Appl. No.: 91,041

[22] Filed: Nov. 5, 1979

[51] Int. Cl.³ .......................... C12N 9/50; C12N 9/48
[52] U.S. Cl. .................................... 435/219; 435/212; 435/816
[58] Field of Search ................................ 435/212, 219

[56] References Cited

U.S. PATENT DOCUMENTS

| | | | |
|---|---|---|---|
| 3,442,764 | 5/1969 | Young et al. ........................ | 435/219 |
| 3,446,626 | 5/1969 | McAnelly et al. ............... | 435/219 X |
| 3,446,706 | 5/1969 | Beuk ................................. | 435/219 X |
| 4,197,291 | 4/1980 | Klein ................................. | 435/212 X |

OTHER PUBLICATIONS

Silverstein et al., "In Vitro Evaluation of Enzymatic Debridement of Burn Wound Eschar", Surgery, vol. 73, No. 1, pp. 15–22, (Jan. 1973).

Levine et al., "Debridement of Experimental Skin Burns of Pigs with Bromelain, a Pineapple Stem Enzyme", Plastic and Reconstr. Surg., vol. 52, No. 4, pp. 413–424 (Oct. 1973).

Levenson et al., "Chemical Debridement of Burns", Ann. Surg., vol. 180, No. 4, pp. 670–704 (1974).

Primary Examiner—Lionel M. Shapiro
Attorney, Agent, or Firm—Cruzan Alexander; Donald M. Sell; Carolyn A. Bates

[57] ABSTRACT

A process is disclosed for isolating an enzyme mixture useful in the treatment of devitalized tissue from crude bromelain. The process comprises the steps of: (1) suspending the crude bromelain in a weakly basic buffer, preferably sodium borate buffer, to selectively dissolve the active enzyme mixture; (2) separating the undissolved solids from the solution; and (3) removing small molecules having a molecular weight of 10,000 or less from the solution.

15 Claims, No Drawings

PROCESS FOR ISOLATING ACTIVE DEBRIDING AGENT FROM BROMELAIN

This invention relates to a process for the isolation of a product from stem bromelain useful in the digestion and dissection of devitalized tissue.

The presence of a proteolytic enzyme or enzymes in the stem of the pineapple plant has long been known. The acetone precipitate from the stem juice which is called stem bromelain has been commercially available for a number of years. It has been the subject of extensive investigation to determine not only its chemical composition, but also its usefulness for a variety of medical and industrial purposes.

Stem bromelain is a crude mixture of many colloids (including proteins, carbohydrates and mucopolysaccharides), inorganic salts and simpler organic materials which are precipitated from the juice of the pineapple stem by acetone. Protein generally constitutes about 50% of the total weight of the dried precipitate, inorganic materials, principally cations (calcium, magnesium, potassium, copper and iron) generally make up to 10–15% of the total weight. The balance is assumed to be complex carbohydrate materials of the nature of polyuronides and glycosides. Crude stem bromelain demonstrates considerable enzymatic activity including proteolytic and acid phosphatase activities and lesser peroxidase, amylase and pectin esterase activities.

Because of its high level of protease activity, crude stem bromelain has been used with varying degrees of success in the debridement of devitalized tissue such as burn eschar in mammals. The object, of course, of enzymatic debriding procedures is to dissolve or digest the devitalized tissue and enable it to be removed from the underlying healthy tissue with a minimum of bleeding and damage to the healthy tissue and to leave behind a graftable bed. Those investigators who have reported on the use of stem bromelain as a debriding agent include Silverstein et al, "In Vitro Evaluation of Enzymatic Debridement of Burn Wound Eschar", *Surgery*, Vol. 73, No. 1, pp. 15–22 (1973); Levine et al, "Debridement of Experimental Skin Burns of Pigs with Bromelain, a Pineapple-Stem Enzyme", *Plastic and Reconstr. Surg.* Vol. 52, No. 4, pp. 413–424 (1973); and Levenson et al, "Chemical Debridement of Burns" *Ann. Surg.*, Vol. 180, No. 4, pp. 670–704 (1974). Most of the foregoing work was done using commercially available stem bromelain in a vehicle such as an oil-in-water emulsion. Results with crude bromelain as a debriding agent, however, have been generally inconsistent and non-reproducible. As a result some efforts have been made heretofore to isolate the active debriding agent from crude bromelain. Levenson et al, supra, fractionated commercial bromelain using various physico-chemical techniques in an attempt to isolate and characterize the active debriding fraction or fractions. According to their isolation technique, commercial bromelain was partially solubilized in Tris-Buffer, pH 7.4, and placed on Sephadex G-100 columns and eluted with Tris-Buffer, pH 7.4, or alternatively, DEAE ion exchange columns were used and elution was with 0.02 M and 0.5 M sodium citrate, pH 6.0. In each case, the proteolytic activity of the various fractions against casein, the ability to attack burn eschar in vitro, and nitrogen content correlated closely. Amylase activity was also present in these fractions indicating more than one enzyme was likely present in each of the collected fractions showing debriding activity.

A more refined attempt to isolate the active debriding agent from commercial stem bromelain was carried out by Klein and Houck. In pending U.S. patent application Ser. No. 887,607 filed Mar. 17, 1978, U.S. Pat. No. 4,197,291, issued Apr. 8, 1980 (South African Pat. No. 77/0209), Klein and Houck describe a process for isolating what they believe to be the active debriding component of stem bromelain. According to their process, crude commercially-available bromelain is extracted into acetate buffer (0.1 M, pH 5.5) which has been made up to 1% in thioglycolic acid. This solution (pH about 4) is then expressed through an ultrafilter and concentrated. The resulting solution is: (1) treated with acetone to precipitate an active fraction; or (2) dialyzed, centrifuged and freeze dried; or (3) subjected to molecular exclusion chromatography as a phenylmercuric salt and further purified by isoelectric focusing. The products obtained by Klein and Houck are characterized as water-soluble, heat-labile, free of caseinolytic activity, having a peak isolectric point at 6, a peak in the ultraviolet region of the spectrum at 280 nm, comprising at least two subunits, each with a molecular weight of from 14,300 to 15,000 daltons, and being capable of dissecting devitalized tissue.

The process of the present invention differs significantly from prior art processes for isolating the active debriding component or mixture of components from commercially-available stem bromelain. A primary novel feature of the process involves the step of selectively solubilizing the active components in a weakly basic buffer. The process results in unexpectedly high yields of a product having superior activity as a debriding agent.

According to the present invention commercially available stem bromelain is suspended in a solution of a weakly basic buffer having a pH of about 8 to 10.5 to selectively solubilize the active components. Undissolved solid is then removed from the suspension by conventional techniques. The solution obtained is further purified to remove small molecules having a molecular weight of about 10,000 or less to form a solution of the active component in water. Further optional steps include removal of the water-insoluble products formed in the preceding purification step, concentration of the solution by reducing the water content, sterilization and lyophilization.

The crude bromelain useful as a starting material for the process of the present invention is available commercially, for example:

"Dole Bromelain 1200" available from Castle & Cooke Foods, P.O. Box 3380, Honolulu, Hawaii.
and "Bromelain" available from Tai Li Enzymes Industrial Co., Ltd., Taiwan.

Commercially available bromelain is known to be prepared from the stem of the pineapple plant. The juice from the stem is first adjusted to a pH of about 3 or 4 with phosphoric acid, and sodium sulfhydride is added to protect against sulfhydryl oxidation. The inert material is precipitated in about 30% acetone (addition of sufficient acetone so that the solution is 30% in acetone) or other suitable solvent and, after filtration, the clarified fluid is precipitated with 70% acetone. This precipitate is collected by centrifugation and either redissolved in water containing sodium sulfhydride which has been acidified with phosphoric acid and reprecipitated, or dried in a vacuum oven directly. If the material is reprecipitated, 70% acetone is generally utilized. The dried material from either process is suitable as a starting material for the process of the present invention.

In the first step of the process, the crude bromelain is suspended in a weakly basic buffer solution. Aqueous buffers are preferred to minimize denaturization of the active enzymes, although other solvents which do not adversely affect the activity of the enzymes could be used. Of the weakly basic buffers, sodium borate is preferred, but other buffers which are acceptable include those with a pKa of about 8 to 10.5 such as disodium phosphate, trishydroxymethylaminomethane hydrochloride, sodium glycylglycine, sodium glycinate, glycinamide hydrochloride, cyclohexylaminoethanesulfonic acid and cyclohexylaminopropane sulfonic acid.

Borate buffers are especially preferred because they temporarily inhibit enzymatic activity of the mixture, producing less reaction with naturally present enzymes and other substrates. This results in less darkening and tarring of the mixture and avoids the usual loss of some enzymatic activity.

The strength of the buffering solution is generally 0.01 to 1.0 M and is preferably 0.01 and 0.2 M. The concentration of the preferred buffer, sodium borate, is limited by low solubility at room temperature and below. The temperature of the solution is generally maintained below 20° C., and preferably below 10° C., to minimize denaturization of the active enzymes. The ratio of buffer solution volume (milliliters) to weight of crude bromelain (grams) is generally from 5 to 1 to 40 to 1 and is preferably from 8 to 1 to 12 to 1.

The buffering solution dissolves substantially all of the desired active enzymes. Generally, the solution is stirred for a period of 2 to 4 hours for maximum solubilization. The undissolved material is then removed by conventional methods such as filtration or centrifugation. The primary criterion for the separation method is that the resulting solution be suitable for the next step, which involves the removal of small molecules having a molecular weight of about 10,000 or less. The presently preferred method of separation is by pressure filtration using a filter aid, e.g., cellulose filter aid, to minimize problems associated with the sticky, gelatinous residue clogging the filtering apparatus.

The removal of the small molecules from the resulting solution can be accomplished using conventional techniques such as dialysis or diafiltration. Diafiltration is preferred for large scale production.

When the filtrate is dialyzed, water is generally used on one side of the dialysis membrane with the filtrate on the other in a volume to volume ratio of 1 to 10, filtrate to water. Dialysis is continued until a substantial portion of the small molecules has been removed; usually about five dilutions is sufficient. Measurement of the optical density at 280 nm of the dialysate is a convenient indicator of the end point of dialysis. Alternatively, the anthrone method of sugar measurement, the end point is about 800 μg/ml.

Although not necessary to enhance the debriding activity of the product, it may be desired for purposes of characterization of the product to subject the solution obtained from dialysis to a cationic exchange process. If this is contemplated, a weakly basic buffer such as boric acid may be used instead of water as the dialyzing fluid. The concentration of the dialyzing fluid in that case is generally 0.01 to 1.0 M, and is preferably 0.02 to 0.75 M. The pH of the solution is generally 7.5 to 9.5, and is preferably 8.0 to 9.0. The purpose of dialysis versus a weakly basic buffer is to remove small molecules from the solution and to obtain a sample which is suitable for ion exchange. In a typical ion exchange process, a cationic exchange resin, e.g., Sephadex CM-50 (a hydrophilic dextran polymer with carboxymethyl groups attached giving the polymer a negative charge, obtained from Pharmacia, Piscataway, N.J.) is used, eluting first with 0.05 M boric acid, pH 8.5, then with a stronger ionic strength buffer, e.g., making the borate buffer 0.25 M in sodium chloride solution. The resin may be used in either batch or column style. The eluate obtained is dialized against water to remove borate and sodium chloride.

During dialysis, buffering material diffuses out and some finely-divided, water-insoluble precipitates form which are desirably removed from solution by conventional methods such as filtration or centrifugation prior to preparing the solution for use or storage. The solution is preferably lyophilized to stabilize the active ingredients until the time of use. At some point prior to use, either before or after lyophilization, the product must be sterilized to avoid contaminating the wound with microorganisms. Conventional sterilization techniques which do not measurably affect the activity of the enzymes such as passage through a Millipore® filter may be used.

When preparing large batches of product it is preferred to remove the small molecules from the buffer solution by diafiltration instead of dialysis. The preferred method of diafiltration involves forcing the filtrate under pressure through a cartridge containing hollow fibers. As the filtrate flows along the thin channel inside each fiber, small molecules and water pass out of the fiber. To compensate for the water which is lost through the fibers, water is added during the process to maintain the retentate volume at the original volume of the starting solution. Diafiltration apparatus of this type is available from Amicon Corporation (Scientific Systems Division, Lexington, Mass.) and Romicon, Inc. (100 Cummings Park, Woburn, Mass.). Hollow fiber cartridges designed to remove small molecules having a molecular weight of about 10,000 or less are used.

Diafiltration is continued until a substantial portion of the small molecules is removed. It has been found that on the equipment used, the diafiltration step is sufficiently complete when the diafiltrate volume is about three times the retentate volume. However, this ratio may vary with the characteristics of the equipment used.

A convenient indicator of the progress of diafiltration can be obtained by a number of analytical tests on the diafiltrate: (1) optical density at 260 nm and 280 nm, which should be at least 0.99 and 1.15, respectively when measured against a water blank; (2) M. Dubois phenol-sulfuric acid method of sugar determination using 100 g/ml galactose as a standard (*Anal. Chem.*-28, p. 350 (1956) which should be at least 800 μg/ml; and (3) Ninhydrin protein determination (Worthington Enzymes (1972), pp. 138-139) using 2 mM leucine as a standard which should be at least 2.4 mM. However, the best method of determining when to cease diafiltration is by careful analysis of the retentate. Values similar to those given in Example 3 below indicate diafiltration can be stopped.

Like dialysis, diafiltration produces some finely-divided, water-insoluble precipitates which may gradually clog the hollow fiber pores. Intermittent separation of these precipitates may be necessary. This is preferably done by shunting the retentate through an auxillary centrifugation or filtration apparatus during the diafiltration process so that complete interruption of diafiltration is not necessary.

After diafiltration is completed, it is desirable to concentrate the solution prior to lyophilization. This is preferably accomplished by passing the solution through the hollow fiber apparatus again, but this time without replacing water. This mode of operating the apparatus to concentrate the solution is termed ultrafiltration.

The concentrated solution obtained through ultrafiltration is preferably lyophilized to maintain stability. A solid product in a yield of about 20 to 40% is provided. Alternatively, the concentrated solution is filtered under sterile conditions to provide a sterile solution which is packaged in a vial which may by lyophilized to provide a sterile powder.

The product obtained by the process of the invention exhibits protease activity against azoalbumin, collagenase activity, and catechol oxidase activity against isoproterenol. It has been found to aid in the removal of devitalized tissue such as burn eschar from mammals. Its method of use for this purpose is described in detail in copending application Ser. No. 91,040 filed on even date herewith and incorporated herein by reference.

The invention is further illustrated by reference to the following non-limiting examples.

EXAMPLE 1

Crude bromelain (20 g obtained from Dole Co., San Francisco, Calif.) is suspended in 200 ml of cold (0° to 5° C.) aqueous 0.075 M sodium borate ($Na_2B_4O_7$) solution (pH 9.4) to provide a solution of pH 8.3 and stirred at 4° C. for three hours. The suspension obtained is separated on a centrifuge at 14,000 times g for 30 minutes at 2° C. The residue is discarded, and the supernatant is dialyzed exhaustively against 0.05 M boric acid ($H_3BO_4$), pH 8.5 (brought to desired pH with sodium hydroxide). A precipitate is formed during dialysis which is removed by centrifugation at 14,000 times g for 30 minutes at 10° C. The supernatant is applied to 10 g of Sephadex CM-50 and equilibrated with 0.05 M boric acid, pH 8.5. This ion exchange step can be carried out using either column or batch methods. Part of the product is eluted by borate buffer, while the remainder of the desired fraction is eluted by making the borate buffer 0.25 M in sodium chloride. The combined eluates are dialyzed exhaustively against pure water to remove borate and sodium chloride. The dialysate is then lyophilized. The yield is 5.4 g of the desired product.

EXAMPLE 2

To a clean 10-gallon glass-lined Pfaudler reactor was added 38 L of ultrapure water containing 1087 g of sodium borate, 10 hydrate ($Na_2B_4O_7.10\ H_2O$). Ultrapure water was obtained by treatment of building-supplied distilled water with a Millipore "Super Q Ultrapure Water System." The water was pumped in series through a carbon filter, ion exchange filter, and a 0.22 $\mu M$ filter. Purity was measured by resistance and equaled 18 megohm-cm or better. The solution was cooled to 5° C. and 3.80 kg of crude Dole bromelain was added in portions over 10 minutes. The reactor stirrer was maintained at 120 rev/min during the addition and for 15 minutes thereafter. The stirring rate was decreased to 80 rev/min and the reactor was purged with nitrogen. The slurry was stirred for 195 minutes. Cellulose filter aid prewashed in ultrapure water (570 g) was added to the reactor and the mixture slurried for several minutes. The mixture was pressured, using nitrogen (5–10 psi), through a jacketed stainless steel "Sparkler" filter containing cellulose filter pads previously treated with 570 g of washed cellulose filter aid. Cold water was circulated through the filter jacket to maintain the internal temperature at 5° C. The filtration slowed quickly requiring 45 minutes for completion. The filter was rinsed with 3.8 1 of 0.075 M $Na_2B_4O_7.10$ $H_2O$ and the combined filtrate was stored in a stainless steel container in a cold room (5° C.) overnight. Examination of the "Sparkler" filter revealed it contained approximately 1 gallon of solution which had not been filtered. Because the solution had warmed to room temperature overnight it was discarded.

The cold aqueous filtrate was transferred to the storage tank of a clean "Romicon" Model HF2SSS ultrafiltration apparatus equipped with two "Romicon" Model HF-15-43-PM-10 hollow fiber cartridges having a molecular weight cutoff of 10,000 and an effective surface area of 15 ft[2]. Each individual hollow fiber has an inside diameter of 43 mil. The "Romicon" apparatus had previously been modified to include two stainless steel heat exchangers, one inserted in front of, and one behind, the cartridges. Diafiltration was started by pumping the solution through the hollow fiber cartridges at 15 psi. The back pressure, or pressure of the solution as it exits in the end of the hollow fibers, was adjusted to 10 psi. The initial temperature of the solution increased to 10° C. but cooling water circulating in the heat exchangers quickly decreased the temperature to 4° C. The diafiltrate solution forced through the hollow fiber walls was collected in a separate tank. The volume of the circulating solution (or retentate) was maintained at 10 gallons through periodic addition of chilled ultrapure water. Samples of the diafiltrate beginning at 2.5 gallons and at 5-gallon intervals throughout the process were taken for analysis. As expected from previous small scale work, a fine solid began to precipitate from solution, decreasing the rate of diafiltration through the hollow fiber walls. After 6.5 hours, 20 gallons of diafiltrate had been collected, but a very slow diafiltration rate forced a stoppage. The enzyme solution (retentate) was drained from the apparatus and stored overnight in a cold room (5° C.). The apparatus was rinsed with tap water, drained, filled with 5 gallons of a solution containing 1 lb of $Na_2B_4O_7.10$ $H_2O$, and allowed to stand overnight.

The enzyme solution mixed with 1 lb of washed cellulose filter aid was transferred to a clean 10 gallon glass reactor and, through cooling, maintained at 5° C. The solution was pressured with nitrogen (5–10 psi) through a 10 micron filter into a chilled stainless steel container over a 2 hour period. This solution was stored in a cold room (5° C.) overnight. The "Romicon" ultrafiltration apparatus was prepared by backflushing at 10 psi approximately 2.5 gallons of diafiltrate back through the hollow fibers then draining the apparatus. The apparatus was flushed with ultrapure water, drained, and chilled. The filtered enzyme solution was re-added and the diafiltration was continued with the temperature again maintained at 5° C. and the retentate volume maintained at 10 gallons. As diafiltration continued a fine precipitate again formed, slowing the diafiltration rate. The total volume of filtrate increased from 20 to 25 gallons after 3 hours, to 27.5 gallons after 5.5 hours, and to 30 gallons after 7 hours. Previous work on small scale hollow fiber equipment had indicated that the diafiltration was complete after the diafiltrate volume was three times the retentate volume. The enzyme (retentate) solution was drained and stored in a stainless steel container in a cold room (5° C.).

The samples of the diafiltrate were tested by: (1) Absorbance versus water at 260 nm and 280 nm; and (2) Ninhydrin protein determination (Worthington: Enzymes (1972) pp. 138-139; 2 mm leucine as standard). Comparison against a reference solution and previously run small scale runs indicated completion by both the absorbance and ninhydrin protein tests. A sample of the enzyme solution was analyzed for protein, carbohydrate, protease, collagenase, and catechol oxidase content. The values are reported in Example 3 below.

The enzyme solution was transferred to a chilled 10-gallon reactor together with approximately 1 lb of washed cellulose filter aid and pressured with nitrogen (5-10 psi) through a 3-micrometer cotton string filter over a 90-minute period. The filter was rinsed with 1 gallon of ultrapure water and the combined filtrate was stored in a stainless steel container in a cold room (5° C.). A 0.25% sodium azide solution which had been added to the hollow fiber cartridges to prevent spoilage was drained and the apparatus was flushed three times with 10 gallons of water. After the hollow fibers were backflushed with ultrafiltrate, the apparatus was flushed twice with 10 gallons of ultrapure water and drained. The enzyme solution was added and ultrafiltration started. The solution (retentate) was again kept cold, however, the solution volume was not maintained constant as in the diafiltration step, but allowed to concentrate. After 2.5 hours of operation the retentate solution, still clear, had been concentrated to 7.5 gallons and was drained and stored in a cold room for 4 days.

The concentrated enzyme solution was lyophilized on a 10 port center well freeze drier in three runs. To a 5 liter single neck glass round bottom flask was added 1.3 liters of the enzyme solution. The flask was turned in a dry ice bath for 20 minutes to shell freeze the solution on the flask walls. The flask was then placed on the freeze drier under vacuum (0.05 mm Hg). The lyophilization for 13 liters (10 flasks) under vacuum of 0.05-0.4 mm Hg required 63 hours. The resulting light solid was collected except for one flask which had a small amount of wet solid (melt down). This wet solid was removed and discarded and the remaining dry solid from the flask was redissolved in the remaining enzyme solution. The remaining enzyme solution was lyophilized in two runs of 10 liters (1 liter per flask) and 2 liters (0.5 liter per flask) each. The material experienced no melt down and required 46 hours and 23 hours, respectively, for completion. The total collected solid from the three runs yielded, 1,099 g (28.9%) of a light tan low density solid.

EXAMPLE 3

The product obtained after diafiltration and prior to lyophilization by the process of Example 2 was carefully analyzed. It had the following properties:

| | | |
|---|---|---|
| Protein Content (Biuret method as Bovine Serum Albumin) | | 23 mg/ml |
| Neutral Carbohydrate Content (Anthrone method as mannose) | | 0.45 mg/mg protein |
| Protease (azoalbumin substrate) | with R—SH | 27 units/mg protein |
| | no R—SH | 2.7 units/mg protein |
| Collagenase | with R—SH | 7.5 μmole leucine/mg protein |
| | no R—SH | 4.5 μmole leucine/mg protein |
| Catechol Oxidase (isoproterenol substrate) | | 2.1 units/mg protein |

What is claimed is:

1. A process for isolating a product from crude bromelain useful in debriding divitalized tissue in mammals comprising the steps of:
   A. suspending the crude bromelain in a solution of a weakly basic buffer having a pH of about 8 to 10.5 to selectively solubilize the active components;
   B. separating the undissolved solids from the solution; and
   C. removing a substantial portion of the small molecules having a molecular weight of about 10,000 or less from said solution.

2. The process according to claim 1 wherein the strength of said buffer solution is 0.01 to 1.0 M.

3. The process according to claim 1 wherein the strength of said buffer solution is 0.01 to 0.2 M.

4. The process according to claim 1 wherein the pH of said buffer solution is 8.0 to 9.5.

5. The process of claim 1 wherein the ratio of milliliters of said buffer solution to grams of said crude bromelain is from 5 to 1 to 40 to 1.

6. The process according to claim 5 wherein said ratio is from 8 to 1 to 12 to 1.

7. The process according to claim 1 wherein said buffer is a borate salt.

8. The process according to claim 1 wherein said borate salt is sodium borate.

9. The process according to claim 1 further comprising the step of removing a finely devided precipitate formed in step C from said solution.

10. The process according to claim 9 further comprising the step of concentrating the solution obtained in step C.

11. The process according to claim 1 further comprising the step of lyophilization of the solution formed in step C.

12. The process according to claim 1 further comprising the step of sterilizing the product from the process.

13. The process according to claim 1 wherein the removal of said small molecules is carried out by dialysis against water.

14. The process according to claim 1 wherein the removal of said small molecules is carried out by diafiltration.

15. A process for isolating a product from crude bromelain useful in debriding devitalized tissue in mammals comprising the steps of:
   A. suspending the crude bromelain in a solution of a weakly basic buffer having a pHa of about 8 to 10.5 to selectively solubilize the active components;
   B. separating the undissolved solids from the solution;
   C. removing a substantial portion of the small molecules having a molecular weight of about 10,000 or less from said solution;
   D. removing the precipitate formed in step C from the resulting solution;
   E. concentrating said resulting solution; and
   F. lyophilizing said resulting solution.

* * * * *